United States Patent [19]

Klemmensen et al.

[11] 4,229,353
[45] Oct. 21, 1980

[54] (2,2-DISUBSTITUTED VINYL)-γ-BUTYROLACTONES

[75] Inventors: Per D. Klemmensen, Lemvig; Hans Kolind-Andersen, Harboor; Hans B. Madsen, Lemvig, all of Denmark

[73] Assignee: A/S Cheminova, Denmark

[21] Appl. No.: 26,746

[22] Filed: Apr. 3, 1979

Related U.S. Application Data

[60] Division of Ser. No. 922,552, Jul. 7, 1978, abandoned, which is a continuation of Ser. No. 756,906, Jan. 4, 1977, abandoned.

[30] Foreign Application Priority Data

Jan. 21, 1976 [GB] United Kingdom .............. 02380/76
May 25, 1976 [GB] United Kingdom .............. 21631/76

[51] Int. Cl.³ .......................................... C07D 307/32
[52] U.S. Cl. ................................................. 260/343.6
[58] Field of Search ..................................... 260/343.6

Primary Examiner—Norma S. Milestone
Attorney, Agent, or Firm—Watson, Cole, Grindle & Watson

[57] ABSTRACT (2,2-Disubstituted vinyl)-γ-butyrolactones of the formula:

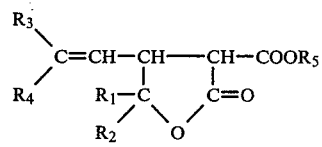

in which
$R_1$ and $R_2$ are hydrogen or $C_1$-$C_6$ alkyl, preferably methyl,
$R_3$ and $R_4$ are hydrogen, $C_1$-$C_6$ alkyl, preferably methyl, or halogen, or, together with the carbon atom to which they are attached, form a cycloalkyl group, and
$R_5$ is $C_1$-$C_6$ alkyl,
are prepared by condensing an epoxide of the formula:

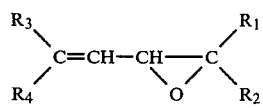

with a malonic acid ester of the formula:

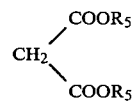

in a basic medium.

The butyrolactones of formula I are valuable intermediates for the synthesis of synthetic pyrethroids having insecticidal activity.

3 Claims, No Drawings

(2,2-DISUBSTITUTED VINYL)-γ-BUTYROLACTONES

This is a division of application Ser. No. 922,552, filed July 7, 1978, which is a continuation of 756,906 filed Jan. 4, 1977, both now abandoned.

This invention is concerned with the preparation of (2,2-disubstituted vinyl)-γ-butyrolactones which are valuable intermediates for the preparation of synthetic pyrethroids having insecticidal activity.

More particularly, the present invention provides a process for the preparation of (2,2-disubstituted vinyl)-γ-butyrolactones of the formula:

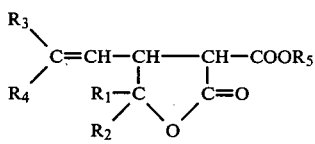

in which $R_1$ and $R_2$, which may be the same or different, are hydrogen or an alkyl group having 1 to 6 carbon atoms, preferably methyl;

$R_3$ and $R_4$, which may be the same or different, are hydrogen, an alkyl group having 1 to 6 carbon atoms, preferably methyl, or a halogen atom, preferably fluorine, chlorine or bromine, or, together with the carbon atom to which they are attached, form a cycloalkyl group; and $R_5$ is an alkyl group having 1 to 6 carbon atoms, preferably ethyl or methyl.

The lactones of formula I may be converted to chrysanthemic acid and its homologues of the formula:

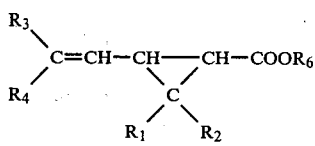

in which $R_6$ is hydrogen or an alkyl group having 1 to 6 carbon atoms and $R_1$, $R_2$, $R_3$ and $R_4$ have the above-stated meanings, by the process described in our British Pat. No. 1,503,857. Such a process, briefly stated with respect to the production of acid esters wherein $R_6$ is an alkyl group having 1 to 6 carbon atoms, involves (a) decarboxylating the lactone of formula I by heating to an elevated temperature in the presence of an inert solvent to obtain a lactone of the formula:

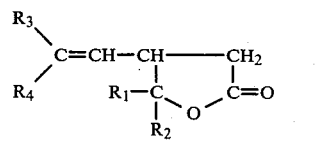

(b) reacting the lactone (IX) with a halogenating or hydrohalogenating agent and with an aliphatic alcohol $R_5OH$, where $R_5$ has the above-stated meaning, to effect ring cleavage, halogenation and esterification to obtain an ester of the formula:

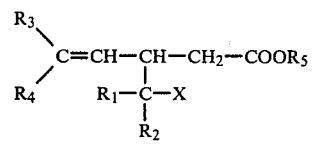

in which X is chlorine, bromine or iodine, and (c) treating the ester (X) with a base to effect dehydrohalogenation and internal condensation such that a formula II chrysanthemic acid ester product is obtained.

The formula II compounds can be directly converted, by esterification or re-esterification, into synthetic pyrethroids of the kind described for example in Nature, 246, Nov. 16, 1973, pages 169-170.

According to the present invention, we provide a process for the preparation of a lactone of formula I, which comprises a condensing an epoxide of the formula:

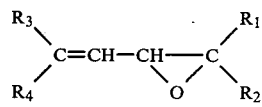

in which $R_1$, $R_2$, $R_3$ and $R_4$ have the above-stated meanings, with a malonic acid ester of the formula:

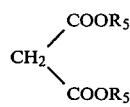

in which $R_5$ has the above-stated meaning, in a basic medium.

In comparison with known processes for the preparation of the compounds of formula I, this process provides a significant improvement in starting material and process economy.

The process is effected in the presence of a base; any suitable organic or inorganic base may be used, preferably sodium ethoxide or methoxide. The process is preferably carried out in the presence of a solvent. The choice of solvent is not critical and any polar or non-polar protic or aprotic solvent may be used, the preferred solvents being alcohols of the formula $R_5OH$, such as ethanol or methanol.

The starting compounds for the process according to the invention, that is the epoxides III, can be obtained in a number of ways. A preferred process for their preparation comprises reacting a diene of the formula:

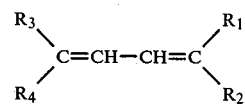

in which $R_1$, $R_2$, $R_3$ and $R_4$ have the above-stated meanings, with a metal oxyhalide, preferably an alkali metal oxyhalide, such as sodium oxychloride, or an alkaline earth metal oxyhalide, such as calcium oxychloride, under alkaline conditions whereby the desired epoxide ring is formed.

The reaction is preferably carried out in the presence of a solvent, preferred solvents for this purpose being water, diethyl ether, toluene and n-heptane. If water is used as the solvent and an alkali metal or alkaline earth metal oxyhalide is used, the necessary basicity for the reaction is generated by the latter during the reaction.

Another method of preparing the epoxides III comprises oxidising a diene of formula V in order to form the desired epoxide ring. The oxidation is preferably effected with a per-acid in the presence of an inert solvent, suitable solvents being, for example, methylene chloride, toluene, n-heptane and glacial acetic acid.

The dienes V can be prepared from readily available starting materials in a number of ways. For the specific case where $R_1$ and $R_2$ are methyl and $R_3$ and $R_4$ are chlorine, a suitable process comprises, for example, the following steps:

(a) reacting chloral with isobutylene (2-methyl-propene) to form

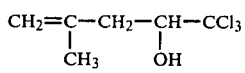

preferably in the presence of aluminium chloride, as catalyst, and a suitable organic solvent, such as hexane, (b) acetylating the product of step (a) to form

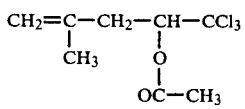

preferably by means of acetic anhydride in the presence of pyridine, (c) dehydrohalogenating the product of step (b) to form

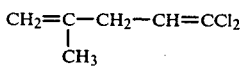

preferably by reaction with zinc and acetic acid in the presence of a suitable organic solvent, such as diethyl ether, and (d) isomerising the product by treatment with an acid, preferably p-toluenesulphonic acid, to obtain the product

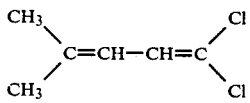

This process, comprising steps (a)–(d), has been described by Farkas et al, Collection Czechoslov. Chem. Commun., 24, (1959), 2230–36.

The necessary variations of this multi-step process required to obtain the other dienes V will be apparent to or readily ascertainable by those skilled in the art.

While it is preferred to use epoxides III as the starting compounds in the process of the invention, it is also possible to use hydroxy-halogen compounds of the formulae:

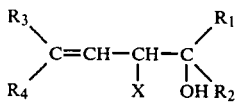

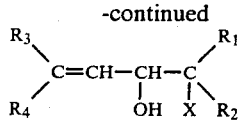

in which $R_1$, $R_2$, $R_3$ and $R_4$ have the above-stated meanings and X is a halogen atom.

When a hydroxy-halogen compound VI or VII is used as the starting compound, it is directly reacted with the malonic acid ester IV under basic conditions, and it is believed that the hydroxy-halogen compound VI or VII is initially converted to the epoxide III when then reacts with the malonic acid ester.

The hydroxy-halogen compounds VI can, for example, be obtained by a variation of the above-described process for preparing the epoxides III in which a diene V is reacted with a metal oxyhalide, preferably sodium oxychloride. In order to obtain the hydroxy-halogen compound VI, the reaction is carried out in the presence of an acid such that the reaction mixture is neutral or acidic; any suitable organic or inorganic acid, for example, sulphuric or acetic acid, may be used for this purpose.

In order that the invention may be more fully understood, the following examples are given by way of illustration only:

EXAMPLE 1

A solution of 67.5 g (0.40 mole) of 1,1-dichloro-3,4-epoxy-4-methyl-1-pentene in 100 ml of absolute alcohol was added to a stirred solution of 10.13 g (0.44 mole) of sodium and 68.87 g (0.43 mole) of diethyl malonate in 900 ml absolute ethyl alcohol at 40° C. and over a period of 25 minutes. The reaction mixture was stirred for 30 minutes, the temperature was then raised to 70° C. and stirring was continued for a further hour. 275 ml of 2 N $H_2SO_4$ were added and the mixture was extracted twice with 500 ml of ethyl ether. The ethereal extracts were combined, dried over anhydrous $MgSO_4$ and evaporated. 200 ml of n-pentane were added and the product, 3-ethoxycarbonyl-4-(2,2-dichlorovinyl)-5,5-dimethyl-γ-butyrolactone, precipitated.

Yield: 70%; M.p. 72.5°–73° C.

Elemental analysis: Calculated for $C_{11}H_{14}O_4Cl_2$: 46.99% C, 5.02% H, 25.22% Cl Found: 46.94% C, 4.99% H, 25.04% Cl.

EXAMPLE 2

The process of Example 1 was repeated, but using dimethyl malonate in place of the diethyl malonate. 3-Methoxycarbonyl-4-(2,2-dichlorovinyl)-5,5-dimethyl-γ-butyrolactone, m.p. 100.6°–101.8° C., was obtained in a yield of 79%.

EXAMPLE 3 (PREPARATION OF EPOXIDE III)

To 30.6 g (0.20 mole) of 1,1-dichloro-1-methyl-1,3-pentadiene in 300 ml of diethyl ether were added an aqueous solution of 0.24 mole of sodium hypochlorite. The reaction mixture was stirred and stirring was continued until the reaction mixture could no longer oxidize iodide ions.

The aqueous phase was saturated with sodium chloride and 200 ml of diethyl ether were added. The phases were separated and the aqueous phase extracted twice with diethyl ether. The ethereal extracts were combined, dried over anhydrous $Na_2SO_4$ and evaporated.

Distillation give 1,1-dichloro-3,4-epoxy-4-methyl-1-pentene in a yield of 50%.

The same result was obtained when 0.24% mole of calcium hypochlorite was used in place of the sodium hypochlorite.

EXAMPLE 4 (PREPARATION OF EPOXIDE III)

To 30.6 g (0.2 mole) of 1,1-dichloro-4-methyl-1,3-pentadiene in 400 ml methylene chloride were added 0.35 mole of technical perchloroacetic acid containing 1.0 g sodium acetate at a temperature of 10°–20° C. over a period of 20 minutes. After stirring for 15 hours, the reaction mixture was poured into 500 ml of water. The phases were separated and the aqueous phase extracted twice with 150 ml of methylene chloride. The organic phases were combined and washed with 10% aqueous sodium carbonate (2×100 ml) and saturated aqueous sodium chloride (1×100 ml), dried over $Na_2SO_4$ and the solvent evaporated. The product was distilled to give 34 g of 1,1-dichloro-3,4-epoxy-4-methyl-1-pentene (82% yield).

Elemental analysis: Calc. for $C_6H_8Cl_2O$: 43.14% C, 4.83% H, 42.45% Cl; Found: 43.14% C, 4.78% H, 42.57% Cl; Boiling point: 41° C./0.4 torr., 59°–60° C./11 torr.

EXAMPLE 5 (PREPARATION OF EPOXIDE III)

The procedure of Example 4 was repeated, but using 0.42 mole of m-chloro-perbenzoic acid in place of the perchloroacetic acid. The product, 1,1-dichloro-3,4-epoxy-4-methyl-1-pentene, was obtained in a yield of 75%.

EXAMPLE 6 (PREPARATION OF DIENE V)

(a) 1,1,1-trichloro-2-hydroxy-4-methyl-4-pentene 11.2 g of liquid 2-methylpropene was added to a solution of 14.7 g of chloral in 50 ml of n-hexane contained in a flask placed in a cooling mixture of ice and salt, the addition being made with stirring. 1.3 g of aluminium chloride was added in small portions to the solution obtained over a period of 1 hour in such a way that the temperature did not exceed 0° C. The mixture was stirred at 0° for another hour, after which 50 ml of water was added, and the mixture was stirred for another 15 minutes. The aqueous layer was separated, the organic layer was washed with water (3×10 ml) dried over $MgSO_4$, and the n-hexane was distilled off.

16.5 g (82%) of 1,1,1-trichloro-4-methyl-4-penten-2-ol, which contained a small amount of isomer as impurity was obtained; b.p. 103°–104° C. 15 mmHg, $n_D 20$ 1.4930, IR spectrum ($cm^{-1}$): 886 ($CH_2C<$), 3100 ($=C-H$), 3410–3540 (assoc. OH).

(b) 1,1,1-trichloro-2-acetoxy-4-methyl-4-pentene

A solution of 1,1,1-trichloro-2-hydroxy-4-methyl-4-pentene (65 g) in pyridine (100 ml) was heated with acetic anhydride (65 ml) at 100° C. for 3 hours. The reaction mixture was poured into water (600 ml) and the resulting solution extracted with ether (3×200 ml). The combined other phases were dried over $MgSO_4$ and the ether was evaporated. Distillation and re-distillation yielded 71.4 g (91%) of 1,1,1-trichloro-2-acetoxy-4-methyl-4-pentene. B.p. 92°–96° C./11 mm Hg.

(c) 1,1-dichloro-4-methyl-1,4-pentadiene

A solution of 65 g of 1,1,1-trichloro-2-acetoxy-4-methyl-4-pentene in 200 ml of ether was added to a stirred suspension of zinc dust (64 g) in 400 ml of ether and 65 ml of acetic acid over a period of 2 hours. The mixture was allowed to reflux for another hour. After filtration, washing with water (300 ml) and with $NaHCO_3$-saturated water, and drying over $MgSO_4$, the ether was distilled off. The remaining mixture was distilled yielding 32.4 g (81%) of 1,1-dichloro-4-methyl-1,4-pentadiene. B.p. 144°–151° C./760 mm Hg.

(d) 1,1-dichloro-4-methyl-1,3-pentadiene 30 g of 1,1-dichloro-4-methyl-1,4-pentadiene were heated with 0.25 g of p-toluenesulphonic acid at 130° C. for an hour. The mixture was directly distilled to give 28.9 g (96%) of 1,1-dichloro-4-methyl-1,3-pentadiene. B.p. 110° C./130 mm Hg.

What is claimed is:

1. A (2,2-Disubstituted Vinyl)-γ-butyrolactone of the formula:

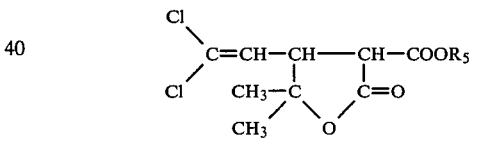

in which $R_5$ is $C_1$ or $C_2$ alkyl.

2. A (2,2-Disubstituted vinyl)-γ-butyrolactone as defined in claim 1 wherein $R_5$ is methyl.

3. A (2,2-Disubstituted vinyl)-γ-butyrolactone as defined in claim 1 wherein $R_5$ is ethyl.

* * * * *